US007354411B2

(12) United States Patent
Perry et al.

(10) Patent No.: US 7,354,411 B2
(45) Date of Patent: Apr. 8, 2008

(54) GARMENT DETECTION METHOD AND SYSTEM FOR DELIVERING COMPRESSION TREATMENT

(75) Inventors: Mathew J. Perry, East Greenwich, RI (US); Mark A. Vess, Hanson, MA (US); Scott Wudyka, Leominster, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 370 days.

(21) Appl. No.: 11/143,548

(22) Filed: Jun. 2, 2005

(65) Prior Publication Data

US 2005/0222526 A1 Oct. 6, 2005

Related U.S. Application Data

(63) Continuation-in-part of application No. 10/784,323, filed on Feb. 23, 2004.

(51) Int. Cl.
*A61F 5/00* (2006.01)

(52) U.S. Cl. ........................................ 602/13; 601/151

(58) Field of Classification Search .................... 602/5, 602/13, 128, DIG. 20; 601/150, 151, 152
See application file for complete search history.

(56) References Cited

U.S. PATENT DOCUMENTS

| | | | |
|---|---|---|---|
| 3,307,533 | A | 3/1967 | Meredith et al. |
| 3,728,875 | A | 4/1973 | Hartigan et al. |
| 3,811,431 | A | 5/1974 | Apstein |
| 3,892,229 | A | 7/1975 | Taylor et al. |
| 3,924,613 | A | 12/1975 | Beck |
| 4,013,069 | A | 3/1977 | Hasty |
| 4,030,488 | A | 6/1977 | Hasty |
| 4,077,402 | A | 3/1978 | Benjamin, Jr. et al. |
| 4,091,804 | A | 5/1978 | Hasty |
| 4,156,425 | A | 5/1979 | Arkans |
| 4,198,961 | A | 4/1980 | Arkans |
| 4,207,876 | A | 6/1980 | Annis |
| 4,253,449 | A | 3/1981 | Arkans et al. |
| 4,396,010 | A | 8/1983 | Arkans |
| 4,408,599 | A | 10/1983 | Mummert |
| 4,419,988 | A | 12/1983 | Mummert |
| 4,469,099 | A | 9/1984 | McEwen |
| 4,481,937 | A | 11/1984 | Arkans |
| 4,501,280 | A | 2/1985 | Hood, Jr. |
| 4,624,244 | A | 11/1986 | Taheri |
| 4,865,020 | A | 9/1989 | Bullard |
| 5,007,411 | A | 4/1991 | Dye |
| 5,022,387 | A | 6/1991 | Hasty |

(Continued)

FOREIGN PATENT DOCUMENTS

| | | | |
|---|---|---|---|
| WO | 0197747 | A1 | 12/2001 |

*Primary Examiner*—MIchael A. Brown
(74) *Attorney, Agent, or Firm*—Edward S. Jarmolowicz

(57) ABSTRACT

A compression treatment system is provided that detects the number of and type of garments connected thereto. The system includes a plurality of ports, valves connected thereto and a number of garments having one or more bladders. The bladders are in fluid communication with a fluid source in a pneumatic circuit, to provide compression therapy once a user confirms the number of and type of garments connected to the system for use by a patient. A single pressure sensor communicates with a plurality of detected bladders located in the one or more garments.

3 Claims, 6 Drawing Sheets

U.S. PATENT DOCUMENTS

| | | | |
|---|---|---|---|
| 5,027,797 | A | 7/1991 | Bullard |
| 5,031,604 | A | 7/1991 | Dye |
| 5,052,377 | A | 10/1991 | Frajdenrajch |
| 5,060,654 | A | 10/1991 | Malkamaki et al. |
| 5,109,832 | A | 5/1992 | Proctor et al. |
| 5,186,163 | A | 2/1993 | Dye |
| 5,254,087 | A | 10/1993 | McEwen |
| 5,301,676 | A | 4/1994 | Rantala et al. |
| 5,307,791 | A | 5/1994 | Senoue et al. |
| 5,383,894 | A | 1/1995 | Dye |
| 5,437,610 | A | 8/1995 | Cariapa et al. |
| 5,502,377 | A | 3/1996 | Freund |
| 5,524,087 | A | 6/1996 | Kawamura et al. |
| 5,556,415 | A | 9/1996 | McEwen et al. |
| 5,575,762 | A | 11/1996 | Peeler et al. |
| 5,588,955 | A | 12/1996 | Johnson, Jr. et al. |
| 5,591,200 | A | 1/1997 | Cone et al. |
| 5,607,447 | A | 3/1997 | McEwen et al. |
| 5,626,556 | A | 5/1997 | Tobler et al. |
| D384,159 | S | 9/1997 | Tsai |
| 5,681,339 | A | 10/1997 | McEwen et al. |
| 5,711,760 | A | 1/1998 | Ibrahim et al. |
| 5,769,797 | A | 6/1998 | Van Brunt et al. |
| 5,830,164 | A | 11/1998 | Cone et al. |
| 5,843,007 | A | 12/1998 | McEwen et al. |
| 5,855,589 | A | 1/1999 | McEwen et al. |
| 5,876,359 | A | 3/1999 | Bock et al. |
| 5,911,735 | A | 6/1999 | McEwen et al. |
| 5,931,853 | A | 8/1999 | McEwen et al. |
| 5,935,146 | A | 8/1999 | McEwen et al. |
| 5,951,502 | A | 9/1999 | Peeler et al. |
| 6,001,119 | A | 12/1999 | Hampson et al. |
| 6,007,559 | A | 12/1999 | Arkans |
| 6,036,662 | A | 3/2000 | Van Brunt et al. |
| 6,051,016 | A | 4/2000 | Mesaros et al. |
| 6,171,254 | B1 | 1/2001 | Skelton |
| 6,231,532 | B1 | 5/2001 | Watson et al. |
| 6,290,662 | B1 | 9/2001 | Morris et al. |
| 6,296,617 | B1 | 10/2001 | Peeler et al. |
| 6,315,745 | B1 | 11/2001 | Kloecker |
| D452,570 | S | 12/2001 | Since |
| 6,436,064 | B1 | 8/2002 | Kloecker |
| 6,440,093 | B1 | 8/2002 | McEwen et al. |
| 6,450,966 | B1 | 9/2002 | Hanna |
| 6,450,981 | B1 | 9/2002 | Shabty et al. |
| 6,468,237 | B1 | 10/2002 | Lina |
| 6,475,228 | B1 | 11/2002 | Mesaros et al. |
| 6,494,852 | B1 | 12/2002 | Barak et al. |
| D473,314 | S | 4/2003 | Since |
| 6,544,202 | B2 | 4/2003 | McEwen et al. |
| 6,572,621 | B1 | 6/2003 | Zheng et al. |
| 6,589,267 | B1 | 7/2003 | Hui |
| 6,629,941 | B1 | 10/2003 | Ishibashi et al. |
| 6,736,787 | B1 | 5/2004 | McEwen et al. |
| 6,786,879 | B1 | 9/2004 | Bolam et al. |
| 6,988,423 | B2 | 1/2006 | Bolam et al. |
| 7,076,993 | B2 | 7/2006 | Cook |
| 2002/0042583 | A1 | 4/2002 | Barak et al. |
| 2002/0042584 | A1 | 4/2002 | Rue |
| 2006/0149176 | A1 | 7/2006 | Bolam et al. |
| 2006/0167389 | A1 | 7/2006 | Evans et al. |

GARMENT DETECTION METHOD AND SYSTEM FOR DELIVERING COMPRESSION TREATMENT

CROSS-REFERENCE TO RELATED APPLICATIONS

This application is a continuation-in-part of U.S. patent application Ser. No. 10/784,323, filed Feb. 23, 2004. The priority of this prior application is expressly claimed and its disclosure is hereby incorporated by reference in its entirety.

BACKGROUND

1. Technical Field

The present disclosure generally relates to the field of vascular therapy for application to a limb of a body, and more particularly, to a compression treatment system having a controller that regulates fluid flow and a method of use thereof.

2. Description of the Related Art

A major concern for immobile patients and persons alike are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popliteal, and tibial return deoxygenated blood to the heart. For example, when blood circulation in these veins is retarded due to illness, injury or inactivity, there is a tendency for blood to accumulate or pool. A static pool of blood is ideal for clot formations. A major risk associated with this condition is interference with cardiovascular circulation. Most seriously, a fragment of the blood clot can break loose and migrate. A pulmonary emboli can form blocking a main pulmonary artery, which may be life threatening.

The conditions and resulting risks associated with patient immobility may be controlled or alleviated by applying intermittent pressure to a patient's limb, such as, for example, a leg including the thigh, calf and foot to assist in blood circulation. Known devices have been employed to assist in blood circulation, such as, one piece pads and compression boots. See, for example, U.S. Pat. No. 6,290, 662 to Morris et al. entitled "Portable, Self-Contained Apparatus For Deep Vein Thrombosis (DVT) Prophylaxis" and U.S. Pat. No 6,494,852 to Barak et al. entitled "Portable Ambulant Pneumatic Compression System."

For example, sequential compression devices have been used, which consist of an air pump connected to a disposable wraparound pad or garment by a series of air tubes. The wraparound pad is configured for placement about a portion of a patient's leg, such as the thigh, calf, or foot. Multiple pads may be mounted to the leg to cover the various portions of the leg. Air is then forced into different parts of the wraparound pad(s) in sequence, creating pressure around the thigh, calf, or foot, thereby improving venous return.

These known devices may suffer from various drawbacks due to their bulk and cumbersome nature of use. These drawbacks reduce comfort, compliance and may disadvantageously prevent mobility of the patient as recovery progresses after surgery.

Further, such known sequential compression devices typically include a controller assembly that regulates air flow and pressure in the wraparound pad(s). The controller assembly can be mounted to a bed and plugged into a wall outlet for power during use. This arrangement, however, can present challenges for example, when the patient needs to perform certain tasks, e.g., bathroom, physical therapy, etc. In these situations, the pads are usually removed, thus disadvantageously discontinuing vascular therapy. Thus, these controller assemblies suffer from various drawbacks because they do not accommodate patient transport or mobility and are not typically adaptable for inflation of thigh, calf, and foot pads.

Other sequential compression devices and systems are known in the art. U.S. Pat. No. 6,786,879 to Bolam et al., entitled "Gradient Sequential Compression System for Preventing Deep Vein Thrombosis," discloses a gradient sequential compression system to prevent deep vein thrombosis. The system has a controller which includes a plurality of feeder valves pneumatically connected to each of the chambers and a microprocessor-based control unit for opening only one of the feeder valves at a time during an inflation cycle, so that each of the chambers can be independently inflated to predetermined pressure levels. The programming of the system controller can either be performed manually by the user through a display interface or by the use of a universal connecting device that senses the mode of operation associated with a sleeve connected thereto and automatically configures the system controller.

Another sequential compression device is disclosed in U.S. Pat. No. 5,876,359 to Bock et al., entitled "Sequential Compression Device Controller," that is currently owned by the assignee of the present application, Tyco Healthcare Group LP. Bock et al. disclose a controller for applying sequential compression to a limb and includes a variable speed motor connected to a pump and an electronic control circuit to drive the pump motor. The system disclosed in Bock et al. includes a pressure transducer in communication with a manifold and adapted for monitoring sleeve pressure.

Another known system is disclosed in U.S. Pat. No. 6,171,254 to Skelton. Skelton discloses a blood pressure monitoring system for automatic unattended operation. During the inflation of cuff, an initial inflation period is defined between the start time and a predetermined end time. After the predetermined end time, the pressure in the cuff is measured and compared to the initial cuff pressure. A microprocessor determines the difference between the initial pressure and the final pressure over the inflation period and produces a curve for identifying the attached cuff.

U.S. Pat. No. 6,450,966 to Hanna discloses an apparatus and a method for the automatic identification of a given one of a predetermined plurality of cuff assemblies that are connectable to a sphygmomanometer for use in a blood pressure measurement procedure. A cuff assembly has a corresponding gas-flow restrictor which allows pressure measurements during the deflation of a cuff to be correlated for identification. Hanna preferably uses at least two pressure transducers. Similarly, U.S. Pat. No. 5,003,981 to Kankkunen discloses a flow restriction means for identifying a cuff.

In U.S. Pat. No. 4,501,280 to Hood Jr., a cuff size is determined based on the propagation time for an audio pulse to propagate to, through, and back from the cuff that is inflated to a predetermined pressure. The measured time is compared to a predetermined threshold value that correlates the measured time to an adult or pediatric cuff thereby identifying the attached cuff. Similarly, U.S. Pat. No. 5,060, 654 to Malkamaki relates to automatic identification for a cuff using a trigger pulse from a valve to a pressure sensing element followed by measuring the width of a detected pulse.

In U.S. Pat. No. 5,301,676 to Rantala et al., an automatic identification method for the cuff of a sphygmomanometer is disclosed. The cuff is identified by measuring values of pressure in at least two spaced apart locations and determining the difference in the pressure values wherein a difference in pressure identifies a pediatric cuff while no pressure difference signifies an adult cuff.

Therefore, it would be desirable to overcome the disadvantages and drawbacks of the prior art with a compression treatment system having a controller that is adaptable for inflating thigh, calf and foot sleeves and accommodates patient transport and mobility to provide continuous vascular therapy. It would be desirable if the system automatically detects the types of garments connected thereto and having any combination or number of bladders therein. It would be highly desirable if the system included a pneumatic circuit that facilitates pressure monitoring with a single pressure transducer to achieve the advantages of the present disclosure. It is contemplated that the compression treatment system is easily and efficiently manufactured.

SUMMARY

Accordingly, a compression treatment system is provided having a controller that is adaptable for inflating thigh, calf and foot sleeves or garments and accommodates patient transport and mobility to provide continuous vascular therapy for overcoming the disadvantages and drawbacks of the prior art. Desirably, the system automatically detects the types of sleeves and foot cuffs and combinations connected thereto. Most desirably, the system includes a pneumatic circuit that facilitates pressure monitoring with a single pressure transducer to achieve the advantages of the present disclosure. The compression treatment system is easily and efficiently fabricated.

The compression treatment system, in accordance with the principles of the present disclosure, can provide intermittent pneumatic compression for the prevention of DVT. The compression treatment system may also include venous refill detection, as will be discussed, and is compact, quiet, lightweight, and offers battery power. The compression treatment system also has the ability to provide sequential, gradient compression to each limb individually and the flexibility to provide compression to various sleeves, which may, for example, include three bladders. The sleeves may include thigh length tear-away features and knee length sleeves, as will be discussed. In addition, the compression treatment system can provide higher pressure, slow compression to a foot sleeve. The compression treatment system provides uninterrupted DVT prophylaxis as the system is used throughout a treatment facility, and can be worn and used continuously by the patient during the entire period of risk. An example of a tear-away garment is disclosed in U.S. patent application Ser. No. 10/784,706, filed Feb. 23, 2004 and assigned to Tyco Healthcare Group LP.

The compression treatment system may be portable to provide continuous therapy for the patient at risk for DVT. This configuration advantageously facilitates continuous vascular therapy during patient activity and tasks such as, for example, transport for testing, bathroom, physical therapy, etc. Thus, the compression treatment system prevents interruptions in therapy by providing a controller that will run on a battery when it is not plugged in, and will also be comfortable, compact, and light enough to move with the patient as needed.

The compression treatment system includes a controller, tubing sets, and sleeves. For example, the compression treatment system delivers air through the tubing sets to a pair of disposable sleeves, one for each limb. The sleeves can have three bladders each, which correspond to the ankle, calf, and thigh. The compression treatment system independently compresses one of the limbs, left or right. Inflation is alternated between the two limbs when both are connected. Alternatively, only one sleeve can be connected. It is understood the compression treatment system can detect any combination of garments and number of bladders therein connected to one or more ports.

Alternatively, the compression treatment system is used as a slow compression foot device. In this configuration, the compression treatment system includes a pair of single-patient-use, single-bladder disposable foot garments alternative to the sleeves. A single foot garment may also be used. The compression treatment system also provides for employment of a foot garment on a first limb and a sleeve on a second limb.

The compression treatment system includes tubing set connector ports that interlock with the mating geometry on the tubing sets. When the compression treatment system is initially powered, air is delivered through the ports until the system recognizes which ports are connected to a sleeve and what types of sleeves, i.e., leg sleeve or foot garment, are connected to those ports. Compression therapy is delivered to the ports with the appropriate sleeves connected.

For example, the compression treatment system provides clinical parameters for vascular therapy such as an 11-second inflation cycle, followed by a vent period of 20 to 60 seconds, depending on the venous refill measurement. The 11-second compression time is sequential: at 0 seconds a first bladder starts inflating. At 2.67 seconds a second bladder starts inflating, and at 5.67 seconds a third bladder starts inflating. After 11 seconds, all three bladders vent. The pressures during the inflation period must remain gradient with the first bladder being greater than the second bladder, and the second bladder being greater than the third bladder. By way of example, the end of cycle pressures may be 45 mm Hg in the first bladder, 40 mm Hg in the second bladder, and 30 mm Hg in the third bladder. Compression continues in this cyclical pattern until either the compression treatment system is turned off or the controller alarms.

By way of another non-limiting example, the foot compression parameters may include a 5-second inflation cycle followed by the same vent period timing as provided above for the sleeve compression (20-60 seconds). The end of cycle pressure for the foot sleeve will have a set pressure target of 130 mm Hg by the end of the 5-second inflation period.

Venous refill detection may be employed with the compression treatment system. Venous refill detection includes trapping a small amount of air in the second bladder described and monitoring the pressure increase as the veins in the limb of a patient refill with blood. As the compression treatment system reaches set pressure, and every 30 minutes thereafter, the controller measures venous refill and adjusts the vent time between inflation cycles for any individual limb from 20 to 60 seconds. The longer of the venous refill measurements from both limbs will be used to adjust the vent time.

The compression treatment system benefits from several advantages including a battery powered controller that is compact and lightweight for portability. The compression treatment system may also be used with one or two limbs and can provide slow compression to a foot garment. The compression treatment system can also detect the type of sleeve connected and automatically apply the appropriate compression.

The compression treatment system also includes a pneumatic circuit designed for use with the compression treatment system to allow for bladder inflation and pressure monitoring using only one transducer. Pressure monitoring from the manifold-side of the solenoid valves must account for the pressure drop across the valves, but with the added advantage of only requiring one transducer to monitor any connected bladder. This configuration advantageously results in a lower manufacturing cost and reduced maintenance requirements, particularly with regard to transducer calibration.

In one embodiment, in accordance with the principles of the present disclosure, the compression treatment system includes a first bladder that is supported about a limb. A second bladder is also supported about the limb. The bladders are in fluid communication with a fluid source and the bladders are inflated such that the first bladder is inflated for a first time period and the second bladder is inflated for a second time period. The second time period is initiated within the first time period. A single pressure sensor communicates with the first bladder and the second bladder. The pressure transducer is configured to monitor pressure of each of the bladders.

The compression treatment system may include a controller that communicates with the pressurized fluid source and the pressure transducer. The controller is configured to monitor and regulate pressure in the bladders. The controller may be disposed with a housing that is portable. The housing may include a plurality of ports connectable to a plurality of bladders.

The pressure transducer can monitor pressure at each of the plurality of ports to determine if a bladder is connected thereto and sends a representative signal to the controller. The controller may include separate valves that regulate inflation of the bladders. The compression treatment system may define a pneumatic circuit. The pressure transducer may be coupled to the pneumatic circuit and disposed between the pressurized fluid source and the valves in the pneumatic circuit.

The compression treatment system may include a third bladder supported about a foot. The third bladder is in fluid communication with the fluid source and the single pressure sensor communicates with bladders. The pressurized fluid source can alternately inflate the bladders disposed about the limb and the bladder disposed about the foot.

In an alternate embodiment, the compression treatment system includes a first plurality of bladders that are supported about a first limb. A second plurality of bladders are supported about a second limb, the bladders are in fluid communication with a fluid source. A first bladder of the first plurality of bladders is inflated for a first time period and a second bladder of the first plurality of bladders is inflated for a second time period. The second time period is initiated within the first time period.

A first bladder of the second plurality of bladders is inflated for a third time period and a second bladder of the second plurality of bladders is inflated for a fourth time period. The fourth time period is initiated within the third time period. A single pressure sensor communicates with the bladders. The pressurized fluid source may alternately inflate the bladders disposed about the first limb and the bladders disposed about the second limb.

In another alternate embodiment, the compression treatment system includes a first plurality of bladders being supported about a first limb and a second plurality of bladders being supported about a second limb. Each bladder of the first plurality of bladders and the second plurality of bladders having a separate valve in communication therewith. The valves are in fluid communication with a fluid source.

A first valve is open such that a first bladder of the first plurality of bladders is inflated for a first time period and a second valve is open such that a second bladder of the first plurality of bladders is inflated for a second time period. The second time period is initiated within the first time period. A third valve is open such that a third bladder of the first plurality is inflated for a third time period. The third time period is initiated within the second time period.

A fourth valve is open such that a first bladder of the second plurality of bladders is inflated for a fourth time period and a fifth valve is open such that a second bladder of the second plurality of bladders is inflated for a fifth time period. The fifth time period is initiated within the fourth time period. A sixth valve is open such that a sixth bladder of the second plurality is inflated for a sixth time period. The sixth time period is initiated within the fifth time period. A single pressure sensor communicates with the bladders.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, which are described below.

DETAILED DESCRIPTION OF EXEMPLARY EMBODIMENTS

Figure 1:
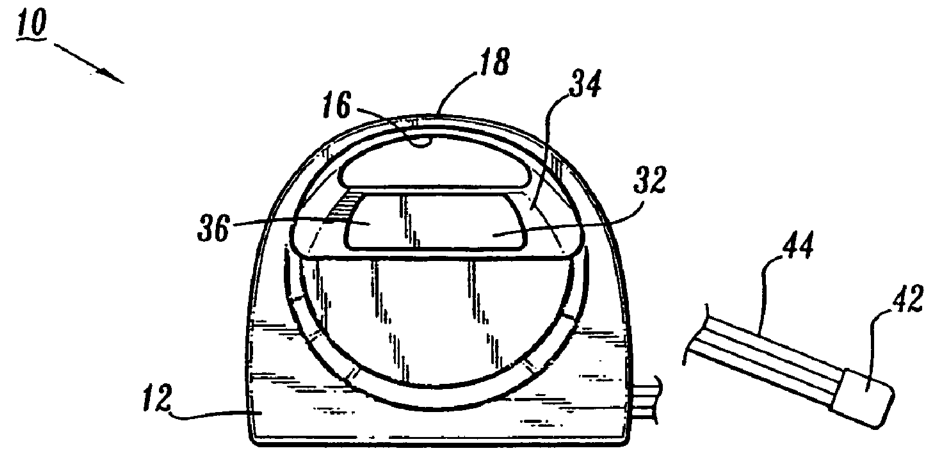
FIG. 1 is a front view of one particular embodiment of a compression treatment system in accordance with the principles of the present disclosure.

The exemplary embodiments of the compression treatment system and methods of operation disclosed are discussed in terms of vascular therapy including a prophylaxis compression apparatus for application to a limb of a body and more particularly in terms of a compression treatment system having a controller that is adaptable for inflating thigh, calf, ankle and foot sleeves and accommodates patient transport and mobility. In particular, the compression treatment system includes a controller, interconnecting tubing, and at least one inflatable garment. The controller includes a pressure transducer, a manifold, and at least one output port adapted for fluidly coupling the controller to the at least one inflatable garment using the interconnecting tubing. The at least one inflatable garment includes at least one inflatable bladder. It is contemplated that the compression treatment system may be employed for preventing and overcoming the risks associated with patient immobility. It is further contemplated that the compression treatment system alleviates the conditions arising from patient immobility to prevent for example, DVT, peripheral edema, etc. It is contemplated that the compression treatment system according to the present disclosure may be attributable to all types of venous compression systems, including, but not limited to a prophylaxis sequential compression apparatus. The term "prophylaxis sequential" shall not be construed as limiting the general venous compression treatment system described herein. It is envisioned that the present disclosure, however, finds application with a wide variety of immobile conditions of persons and patients alike, such as, for example, those undergoing surgery, anesthesia, extended periods of bed rest, obesity, advanced age, malignancy, prior thromboembolism, etc.

In the discussion that follows, the term "proximal" refers to a portion of a structure that is closer to a torso of a subject and the term "distal" refers to a portion that is further from the torso. As used herein the term "subject" refers to a patient undergoing vascular therapy using the compression treatment system. According to the present disclosure, the term "practitioner" refers to an individual administering the compression treatment system and may include support personnel. According to the present invention, the term "garment" is a generic term that includes foot cuff, knee sleeve, or leg sleeve. According to the present invention, the term "chamber" and the term "bladder" are used interchangeably.

The following discussion includes a description of the compression treatment system, followed by a description of an exemplary method of operating the compression treatment system in accordance with the principles of the present disclosure. Reference will now be made in detail to the exemplary embodiments and disclosure, which are illustrated with the accompanying figures.

Turning now to the figures, wherein like components are designated by like reference numerals throughout the several views. Referring initially to FIGS. 1-5, there is illustrated a compression treatment system 10, constructed in accordance with the principles of the present disclosure. Compression treatment system 10 includes a housing 12. Housing 12 encloses the components of a controller 14 (shown schematically in FIG. 5) disposed therein.

Housing 12 has a semi-circular configuration and has a handle cutout 16 along its apex 18 to facilitate transport and subject mobility. It is envisioned that housing 12 may be variously configured and dimensioned such as, for example, rectangular, spherical, etc. It is further envisioned that housing 12 may be assembled by any appropriate process such as, for example, snap fit, adhesive, solvent weld, thermal weld, ultrasonic weld, screw, rivet, etc. Alternatively, housing 12 may be monolithically formed or integrally assembled of multiple housing sections and may be substantially transparent, opaque, etc. Housing 12 may include ribs, ridges, etc. to facilitate manipulation of compression treatment system 10.

The components of housing 12 can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

Figure 2:
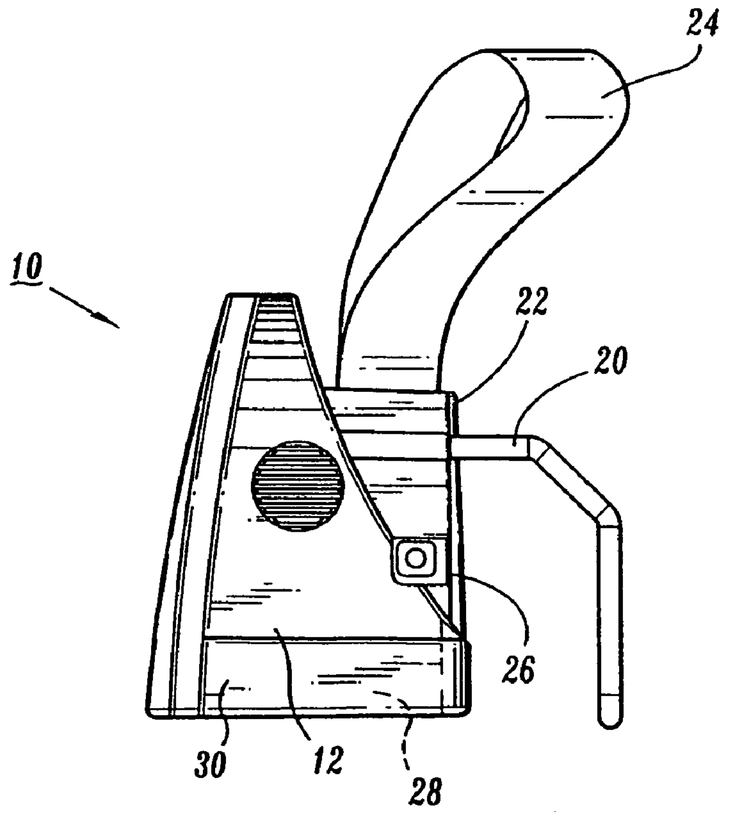
FIG. 2 is a side view of the compression treatment system shown in FIG. 1.

Housing 12 is portable to facilitate continuous vascular therapy to a subject (not shown). Housing 12 includes a bracket 20 that facilitates releasable mounting of housing 12 with for example, a hospital bed, table, etc. Bracket 20 extends from a rear portion 22 of housing 12 and provides a hook configuration for suspending housing 12 from a subject's bed, etc. It is contemplated that bracket 20 may be suspended from various structure for releasable mounting of housing 12, or alternatively, that housing 12 does not include a bracket and may be placed on a floor or other supporting surface. Alternatively, housing 12 includes a shoulder strap 24, as shown in FIG. 2, that allows housing 12 to be worn on the subject or practitioner during transport. Shoulder strap 24 may be employed with or without bracket 20 and may for example, be secured to any portion of the housing 12 including handle 16.

Compression treatment system 10 employs an electrical AC/DC switching power supply for operation of its components. A power cord 26 is connected to housing 12 for conducting power to the components of controller 14. Power cord 26 accesses an AC power supply via a wall outlet, etc. Controller 14 may include a transformer or other electronics for connecting to the power supply. It is envisioned that power cord 26 may be wrapped around bracket 20 for storage and during transport and subject mobility. It is further envisioned that compression treatment system 10 may include a storage capture mechanism that retains power cord 26 with housing 12. The storage capture mechanism may include an elastic cord, pulley, etc.

Compression treatment system 10 also employs a battery 28 (FIG. 2) for powering the components of controller 14 to facilitate transport and subject mobility. Battery 28 is disposed within a battery compartment 30 of housing 12. It is contemplated that battery 28 may include one or a plurality of cells. The battery cells may be lithium-ion type, etc. It is further contemplated that battery 28 is rechargeable and may be employed for various ranges of operation time, such as, for example, 6 hours, 8 hours, 10 hours, etc. For example, power cord 26 may be unplugged and captured by the storage capture mechanism of housing 12. Compression treatment system 10 then runs on battery 28 power and the subject is ambulatory.

It is envisioned that battery 28 may be mounted to an exterior surface of housing 12 or separate therefrom. It is further envisioned that compression treatment system 10 may include alternate sources of power supply, such as, for example, solar, non-electrical, etc., or alternatively may not include battery power.

Figure 1A:
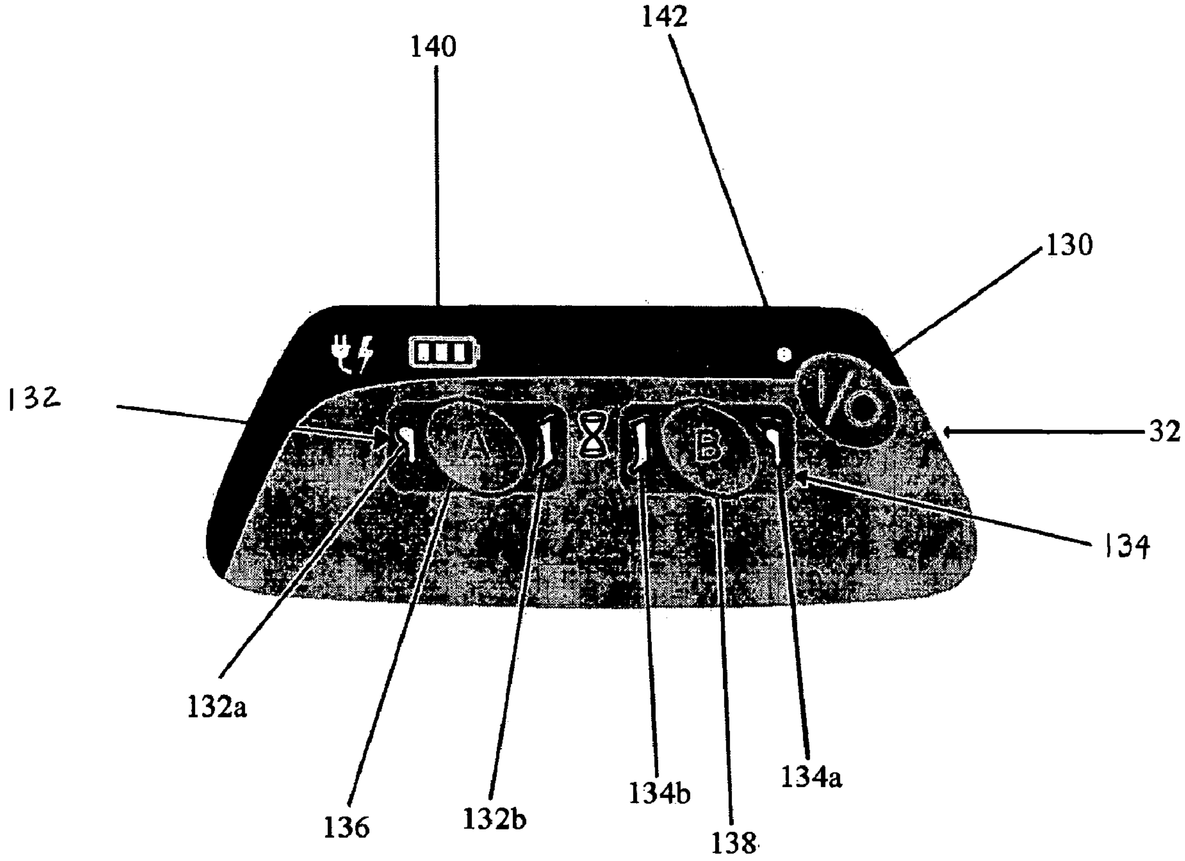
FIG. 1A is a front view of a control panel of the compression treatment system of FIG. 1.
Figure 3:
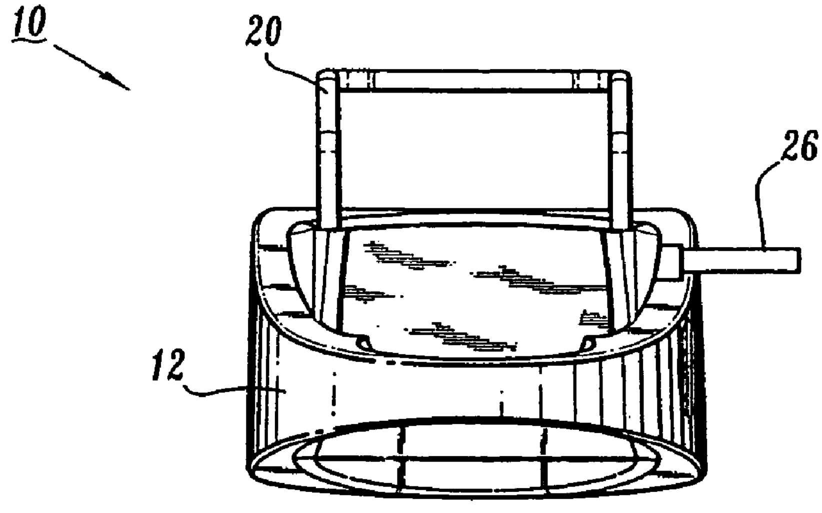
FIG. 3 is a top view of the compression treatment system shown in FIG. 1.

Housing 12 has a control panel 32 disposed on a front surface 34 thereof (FIGS. 1 and 1A). Control panel 32 includes controls and indicators for operation of compression treatment system 10. Control panel 32 has an LED display 36 that provides status indicia, messages, etc. of the various components of system 10, such as, for example, power, battery, sleeve identification and connection, inflation, venting, venous refill, errors, etc. In particular, control panel 32 includes a power switch 130, status indicator 142, battery level indicator 140, port A control 132, and port B control 134. Port A control 132 includes a switch 136 and garment indicators 132*a*, 132*b*. Similarly, port B control 134 includes a switch 138 and garment indicators 134*a*, 134*b*. Control panel 32 also includes manually activated switches for powering system 10, etc. Specifically, compression treatment system 10 is energized using power switch 130 while the operator may confirm the treatment method using switches 136 and/or 138 as will be discussed hereinbelow, It is contemplated that such switches are membrane type actuated by finger pressure, etc.

Figure 4:
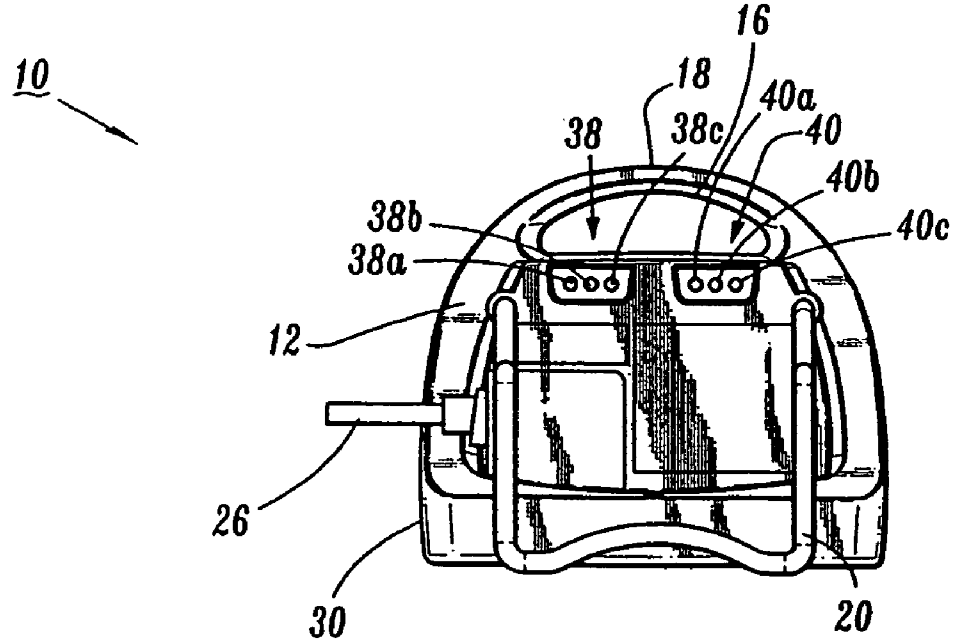
FIG. 4 is a rear view of the compression treatment system shown in FIG. 1.

Rear portion 22 of housing 12 defines ports 38, 40 (FIG. 4). Ports 38, 40 include output ports 38*a*, 38*b*, 38*c*, and output ports 40*a*, 40*b*, 40*c*, respectively. Output ports 38*a*, 38*b*, 38*c*, and output ports 40*a*, 40*b*, 40*c* are in fluid communication with inflatable chambers or bladders 46*a*, 46*b*, 46*c* of a compression sleeve 46 and inflatable chambers or bladders 48*a*, 48*b*, 48*c* of a compression sleeve 48, respectively, which are configured to fit around the legs of a subject, via a mating connector 42 and tubing set 44, as will be discussed. Output ports 38*a*, 38*b*, 38*c*, 40*a*, 40*b*, 40*c* are configured for connection to tubing set 44. Each of ports 38, 40 are connectable to a particular compression sleeve or garment, for example, leg sleeve, foot sleeve, etc.

Figure 5:
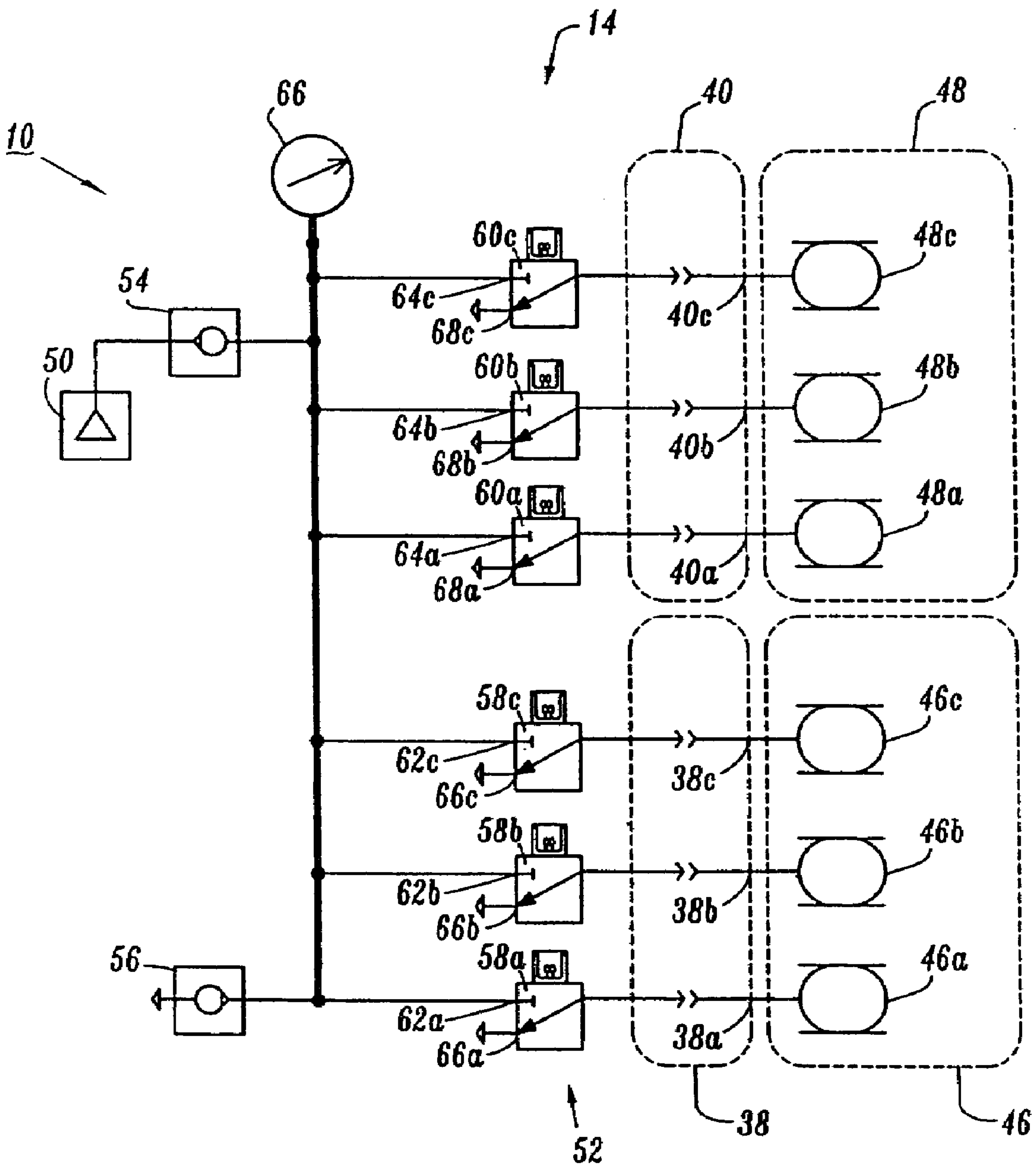
FIG. 5 is a schematic representation of a pneumatic circuit of the compression treatment system shown in FIG. 1.

Ports 38, 40 are also connected with the components of controller 14 disposed within housing 12 to facilitate inflation of selected compression sleeves, as illustrated in the pneumatic circuit shown in FIG. 5. Controller 14 includes a pressurized fluid source, such as, for example, a pump 50 that fluidly communicates with a valve manifold 52 for connection with ports 38, 40, as will be discussed. Pump 50 includes a motor that compresses air to valve manifold 52 via tubing or the like. The speed of the pump motor is electronically controlled to provide a corresponding compressor speed for respective output pressures as desired. Examples of systems including electronically controlled pump motors and associated compressors are disclosed in U.S. Pat. No. 5,876,359 to Bock et al. and U.S. Pat. No. 6,231,532 to Watson et al., both of which are assigned to Tyco Healthcare Group LP and are hereby incorporated by reference in their entirety. It is contemplated that a power supply board, including the necessary electronics, circuitry, software, etc. known to one skilled in the art, is connected to the pump motor and other components of controller 14 to regulate power thereto. It is envisioned that pump 50 may be a diaphragm pump.

Controller 14 also includes a check valve 54 that prevents air leakage back through pump 50 when monitoring bladder pressure during venous refill detection, as will be discussed. A pressure relief valve 56 is disposed with the pneumatic circuit to protect against over pressure in the compression sleeves. Pressure relief valve 56 is configured to bleed excess air pressure if necessary. It is contemplated that various types of valves may be employed such as, for example, spring loaded plunger valves, etc.

Check valve 54 is a mechanical device as is known in the relevant art. In particular, check valve 54 is disposed between pump 50, or an alternate air source, and valve manifold 52. Essentially check valve 54 is disposed between pump 50 and pressure transducer 66. When pump 50 is energized, pressurized air is provided through check valve 54 into valve manifold 52 with minimal restriction to the volumetric flow rate, and then solenoid valves 58*a*, 58*b*, 58*c*, 60*a*, 60*b*, 60*c* can be opened (i.e. energized) and provide pressurized air to the individual bladders of any garments that have been connected to compression treatment system 10 Compression treatment system 10 is adapted to measure static pressure at one of solenoid valves 58*a*, 58*b*, 58*c*, 60*a*, 60*b*, 60*c* or attached bladders by turning off (i.e. de-energizing) pump 50. Substantially simultaneously, check valve 54 will automatically close thereby inhibiting the flow of pressurized air to pump 50 through check valve 54. A substantially fluid tight seal is often not achieved by pump 50 itself, and if pressurized air is allowed to flow back through pump 50 when it is turned off (i.e. partially venting compression treatment system 10), pressure measurements in a connected bladder or in components connected to valve manifold 52 will be biased by the flow of pressurized air and compression treatment system 10 will measure the dynamic pressure rather than the static pressure. Furthermore, any leakage of pressurized air through pump 50 would prevent compression treatment system 10 from maintaining a constant system pressure with pump 50 turned off.

Using a simple check valve, as opposed to an electrical solenoid valve, offers a number of advantages. The check valve does not require any electrical signals and therefore does not consume any electrical energy, which is especially important when operating on battery power. The check valve does not generate heat like an energized solenoid valve. The check valve is typically much quieter and lighter than a solenoid valve.

Valve manifold 52 includes solenoid valves 58*a*, 58*b*, 58*c*, 60*a*, 60*b*, 60*c* that are coupled to output ports 38*a*, 38*b*, 38*c*, 40*a*, 40*b*, 40*c*, respectively. Solenoid valves 58*a*, 58*b*, 58*c*, 60*a*, 60*b*, 60*c* each have an associated solenoid that is electrically driven via a control processor of controller 14. The solenoid is coupled to a valve seat of each particular solenoid valve 58*a*, 58*b*, 58*c*, 60*a*, 60*b*, 60*c* such that the seat is operative to open and close the respective solenoid valve upon actuation of the solenoid. See, for example, the solenoid valves described in U.S. Pat. No. 5,876,359 to Bock et al., the entire contents of which is hereby incorporated by reference herein. It is contemplated that the control processor of controller 14 includes the necessary electronics, circuitry, software, etc. known to one skilled in the art to actuate solenoid valves 58*a*, 58*b*, 58*c*, 60*a*, 60*b*, 60*c* in response to varying conditions of compression treatment system 10 and other indications and measurements sensed by the components of controller 14. It is envisioned that one or a plurality of solenoid valves may be employed, or alternatively, that other types of valves may be used.

Solenoid valves 58*a*, 58*b*, 58*c*, 60*a*, 60*b*, 60*c* and their associated valve components are mounted to ports 38, 40 on the interior of housing 12. Solenoid valves 58*a*, 58*b*, 58*c*, 60*a*, 60*b*, 60*c* are two position, three-way normally closed valves, which have openings 62*a*, 62*b*, 62*c*, 64*a*, 64*b*, 64*c*, respectively. In the open position, air flows through openings 62*a*, 62*b*, 62*c*, 64*a*, 64*b*, 64*c* to the associated output port 38*a*, 38*b*, 38*c*, 40*a*, 40*b*, 40*c* and into inflatable chambers 46*a*, 46*b*, 46*c* of compression sleeve 46 and inflatable chambers 48*a*, 48*b*, 48*c* of compression sleeve 48. In the closed position, openings 62*a*, 62*b*, 62*c*, 64*a*, 64*b*, 64*c* are blocked and air from compression sleeves 46, 48 flows back through output port 38*a*, 38*b*, 38*c*, 40*a*, 40*b*, 40*c* and through vent ports 66*a*, 66*b*, 66*c*, 68*a*, 68*b*, 68*c* of the associated valve to deflate inflatable chambers 46*a*, 46*b*, 46*c*, 48*a*, 48*b*, 48*c*.

Solenoid valves 58*a*, 58*b*, 58*c*, 60*a*, 60*b*, 60*c* are operated in sequence to pressurize inflatable chambers 46*a*, 46*b*, 46*c*, 48*a*, 48*b*, 48*c* and provide sequential pressurization thereof and venting of the chambers under the control processor of controller 14. It is contemplated that solenoid valves 58*a*, 58*b*, 58*c*, 60*a*, 60*b*, 60*c* may be selectively actuated when cooling operation of the sleeves is desired, see for example, U.S. Pat. No. 5,876,359 to Bock et al.

Solenoid valves 58*a*, 58*b*, 58*c*, 60*a*, 60*b*, 60*c* are driven by pulse width modulated signals provided by the control processor of controller 14. The solenoid drive signals are initially at a higher power level for rapid and positive actuation of the solenoid valves. After initial actuation, the drive signals can be decreased, for example, by approximately 70% to maintain valve activation, thereby reducing power consumption. It is envisioned that solenoid valves 58*a*, 58*b*, 58*c*, 60*a*, 60*b*, 60*c* may be deactivated as desired. It is further envisioned that the control processor of controller 14 includes the ability to verify the status of solenoid valves 58*a*, 58*b*, 58*c*, 60*a*, 60*b*, 60*c*. As the condition of solenoid valves 58*a*, 58*b*, 58*c*, 60*a*, 60*b*, 60*c* changes, the control processor verifies their status. For example, if a particular valve is detected to be shorted or open, compression treatment system 10 will go into a particular error mode, as will be discussed.

Controller 14 also includes a single pressure transducer 66 disposed within housing 12. Pressure transducer 66 is coupled to the pneumatic circuit and disposed between pump 50 and solenoid valves 58*a*, 58*b*, 58*c*, 60*a*, 60*b*, 60*c* via tubing or the like. Pressure transducer 66 is in fluid communication with inflatable chambers or bladders 46*a*, 46*b*, 46*c*, 48*a*, 48*b*, 48*c* for monitoring pressure in each of inflatable chambers or bladders 46*a*, 46*b*, 46*c*, 48*a*, 48*b*, 48*c*. The control processor (not shown) of controller 14 directs pressure transducer 66 to detect or monitor a pressure in any of inflatable chambers or bladders 46*a*, 46*b*, 46*c*, 48*a*, 48*b*, 48*c* that are connected to their respective solenoid valve and thus in fluid communication therewith. Disposing pressure transducer 66 before the solenoid valves, on the manifold side of the pneumatic circuit, advantageously facilitates use of only a single pressure transducer for measuring the pressure in the inflatable chambers or bladders. This configuration facilitates inflation or pressure measurement of one or a plurality of inflatable chambers or bladders. This configuration also advantageously reduces bulk of controller 14 to contribute to the compact and lightweight design of compression treatment system 10, facilitates transport, patient mobility, and reduces manufacturing costs.

In particular, pressure transducer 66 is disposed downstream of check valve 54 and upstream of solenoid valves 58*a*, 58*b*, 58*c*, 60*a*, 60*b*, 60*c* as shown schematically in FIG. 5. As will be discussed in detail hereinafter, by disposing a single pressure transducer 66 between check valve 54 and solenoid valves 58*a*, 58*b*, 58*c*, 60*a*, 60*b*, 60*c*, pressure transducer 66 is capable of detecting or monitoring a pressure value in one or more of inflatable chambers 46*a*, 46*b*, 46*c*, 48*a*, 48*b*, 48*c* as selected by an operator or controller 14. Additionally, pressure transducer 66 may monitor a static pressure value in manifold 52 (i.e. solenoid valves 58*a*, 58*b*, 58*c*, 60*a*, 60*b*, 60*c* are in the closed position and pump 50 is not supplying pressurized air to manifold 52) or a dynamic pressure value in manifold 52 (i.e. solenoid valves 58*a*, 58*b*, 58*c*, 60*a*, 60*b*, 60*c* are in the open position and pump 50 is supplying pressurized air to manifold 52). Accordingly, a minimum number of components are required for monitoring pressure values during system 10 operation.

According to an embodiment of the present disclosure, system 10 is adapted for detecting and monitoring various pressure values. For example, with reference to FIG. 6, as bladder 114 is being pressurized, system 10 monitors the pressure of bladder 116 or 118. As mentioned previously, controller 14 in cooperation with pressure transducer 66 selects one or more bladders of the attached inflatable sleeves, static system pressure in system 10, or dynamic system pressure in system 10. Specifically, when measuring a pressure value in an attached sleeve, controller 14 energizes the solenoid valves associated with that sleeve (i.e. solenoid valves are open) and de-energizes the solenoid valves associated with the other sleeve (i.e. solenoid valves are closed). As such, pressure transducer 66 is in fluid communication with the bladders of only the selected sleeve and measures the pressure in only that sleeve. Alternatively, system 10 may detect and/or monitor the pressure in a single bladder of an attached sleeve as follows: controller 14 energizes the solenoid valve associated with the selected bladder to be monitored while de-energizing the solenoid valves for the remaining bladders. Therefore, pressure transducer 66 only measures the pressure of a single bladder in a selected inflatable sleeve. Further still, controller 14 may energize and de-energize different combinations of solenoid valves to detect pressure for the attached inflatable sleeves such that, for example, an average pressure for a sleeve is monitored, an average pressure for both sleeves is monitored, individual bladders in different sleeves are monitored. For example, system 10 energizes solenoid valve 60*c* that is associated with output port 40*c* and inflatable bladder 48*c* (FIG. 5). Controller 14 obtains a pressure value from pressure transducer 66 that corresponds to the pressure value in bladder 48*c* in compression sleeve 48.

Alternatively, controller 14 may de-energize all the solenoid valves (i.e. closing them all) such that pressure transducer 66 monitors pressure in system 10 excluding the inflatable sleeves. This may be done as part of a system leak test, system overpressure test, or other testing as desired. Further still, controller 14 may energize all the solenoid valves such that pressure transducer 66 monitors system 10 pressure including one or more attached inflatable sleeves. This may be done as part of an operational test to monitor dynamic pressure during inflation and/or deflation of the attached inflatable sleeves or during a system leak test.

For example, during a selected compression cycle, solenoid valves 58*a*, 58*b*, 58*c*, 60*a*, 60*b*, 60*c* are sequentially energized to the open position for pressurizing, in sequence, inflatable chambers 46*a*, 46*b*, 46*c*, 48*a*, 48*b*, 48*c*. In the open position, solenoid valves 58*a*, 58*b*, 58*c*, 60*a*, 60*b*, 60*c* allow passage of air from pump 50 through the respective output ports 38*a*, 38*b*, 38*c*, 40*a*, 40*b*, 40*c* to the inflatable chambers. Pressure transducer 66 monitors the pressure of each of inflatable chambers 46*a*, 46*b*, 46*c*, 48*a*, 48*b*, 48*c* of the pneumatic circuit and provides an electrical signal input to the control processor of controller 14 for feedback control.

At the end of the selected compression cycle, solenoid valves 58*a*, 58*b*, 58*c*, 60*a*, 60*b*, 60*c* are simultaneously de-energized to the closed position for disconnecting pump 50 from sleeves 46, 48. In the closed position, pump 50 air is blocked and solenoid valves 58*a*, 58*b*, 58*c*, 60*a*, 60*b*, 60*c* vent sleeve pressure to the atmosphere via vent ports 66*a*, 66*b*, 66*c*, 68*a*, 68*b*, 68*c* on valve manifold 52. It is contemplated that compression treatment system 10 can alternate inflation of the chambers between a first limb and a second limb. It is further contemplated that compression treatment system 10 can individually inflate each bladder.

Figure 6:
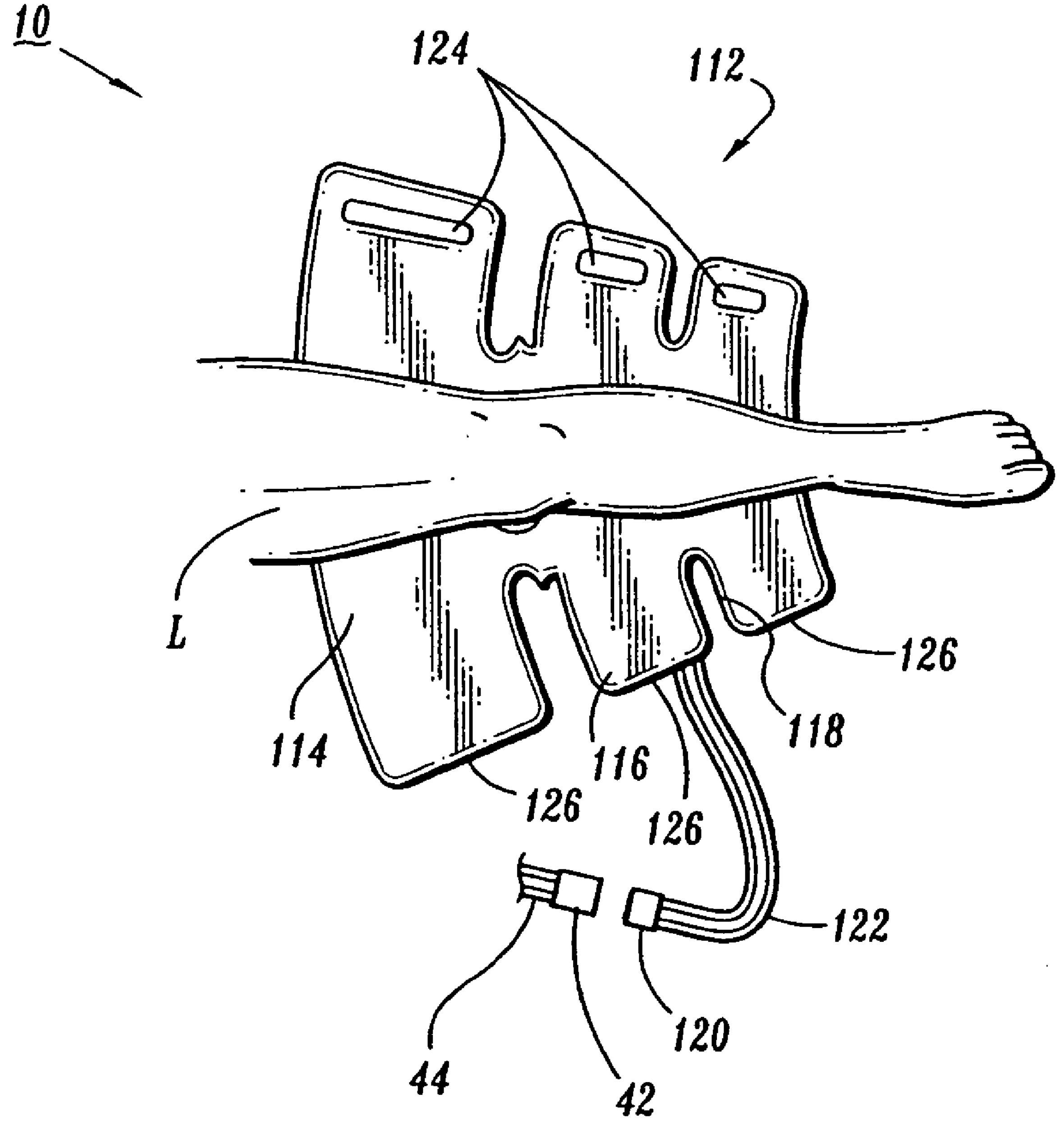
FIG. 6 is a plan view of a sleeve of the compression treatment system shown in FIG. 1 being disposed about a limb.

Referring to FIG. 6, compression treatment system 10, similar to that described above, is assembled and packaged for use. In operation, compression treatment system 10 includes controller 14 disposed with housing 12, described above, and a sleeve 112. Sleeve 112 includes a thigh bladder 114, a calf bladder 116, and an ankle bladder 118. Sleeve 112 includes a connector 120 that mates with mating connector 42, which is connected to port 38 via tubing 44. Connector 120 fluidly communicates with the chambers of sleeve 112 via tubing set 122. Thus, this configuration facilitates fluid communication between bladders 114, 116, 118 and pump

50. It is contemplated herein that connector 120 may further include a valve mechanism to control fluid flow.

Sleeve 112 is provided and manipulated for disposal about leg L of the subject (not shown). Connector 120 is mated with mating connector 42 to establish fluid communication between sleeve 112 and the pneumatic circuit. Sleeve 112 is wrapped about leg L and secured thereto via hook and loop pads 124, 126. It is contemplated that compression treatment system 10 may treat a second leg of a subject with a compression sleeve, similar to sleeve 112, via connection to port 40. The second leg is treated in compression cycles alternate to the compression cycles described below for treatment of leg L, as described below in the alternative.

The portable features of housing 12 and controller 14, described above, provide a compression treatment system 10 that facilitates transport and subject mobility. This advantageous configuration provides uninterrupted DVT prophylaxis as the system is used throughout a treatment facility, and can be worn and used continuously by the subject during the entire period of risk. Compression treatment system 10 advantageously facilitates continuous vascular therapy during subject activity and tasks such as, for example, transport for testing, bathroom, physical therapy, etc. Compression treatment system 10 prevents interruptions in therapy by providing controller 14 that will run on battery 28 when power cord 26 is not plugged in, and will also be comfortable, compact, and light enough to move with the subject as needed.

The manually activated switches of control panel 32 of controller 14 switch compression treatment system 10 on for powering thereof. As compression treatment system 10 is initially switched on, a series of self-tests are conducted by the control processor of controller 14. The LED indicators of display 36 are illuminated and audible indicia are sounded to verify the operability of the visual and audible indicators. Display 36 is illuminated to verify display operability. Controller 14 also verifies operability of the software of the control processor. If any of the verification fails, error codes provide a representative audible and/or visual indicia.

It is contemplated that if the control processor of controller 14 cannot continue normal software execution, an error code will be triggered. This causes compression treatment system 10 to reset and restart normal operation. Sleeve 112 would vent during a restart procedure. Audible and visual indicia may also engage to represent the condition.

Upon completion of the self-test sequence compression for treatment system 10, controller 14 begins a sleeve detection procedure to determine the type(s) of sleeves or garments attached to ports 38, 40. Sleeve or garment detection is performed during a first detection cycle after controller 14 is initially powered on. During the detection cycle, air is delivered alternately through ports 38, 40 with pump 50 operating for two seconds, or until the pressure reaches a default threshold. After a predetermined amount of time, typically one second later, pressure transducer 66 takes a pressure measurement to determine whether or not a bladder is connected to a particular output port, 38*a*, 38*b*, 38*c*, 40*a*, 40*b* or 40*c* under sleeve detection.

For example, the detection procedure is conducted for bladders 114, 116, 118 for each of sleeve ports 38, 40. If there is no backpressure at a particular outlet port for connection with a bladder, then the control processor of controller 14 determines that a bladder is not being used with a particular outlet port. The control processor adjusts the compression therapy for the detected sleeve configuration accordingly. For the 3-bladder sleeve, back pressure is detected at bladders 114, 116, 118 when connected to controller 14. It is contemplated that if no sleeves are detected by this procedure at either port 38 or 40, or if the detected configuration is not recognized, then a low pressure error is triggered with corresponding audible indicia. It is further contemplated that various timing periods may be employed for detection inflation and pressure measurement, according to the requirements of a particular application.

Specifically, during the garment detection cycle, system 10 alternately supplies pressurized air from pump 50 through ports 38, 40 for identifying if a sleeve is attached to either port and also to identify the type of sleeve attached thereto. As discussed hereinabove, pressurized air is supplied to ports 38, 40. Illustratively, one port will be discussed in detail with operation of the other port being substantially similar. In particular, pressurized air is supplied to two of output ports 38*a*, 38*b*, or 38*c* for about two seconds or until the pressure reaches a default threshold as measured by pressure transducer 66. If no backpressure is measured by pressure transducer 66 at a selected output port, system 10 recognizes that the selected output port, and therefore the selected inflatable bladder, is not being used. By way of example, if a foot sleeve is attached to system 10, backpressure should only be measured at one of the two selected output ports since the foot sleeve includes one inflatable bladder.

Alternately, if a leg sleeve is attached to system 10, backpressure should be measured at both selected output ports since the leg sleeve includes at least two inflatable bladders. Therefore, system 10 identifies the number and types of inflatable sleeves attached to ports 38, 40. Further still, system 10 communicates this information to the operator via display 36. Visual indicators on display 36 are illuminated to indicate the number and type of inflatable sleeves attached to system 10 as identified by system 10 during the garment detection cycle. In particular, if a foot cuff is attached to system 10 at either port 38 or 40, system 10 identifies the foot cuff as discussed above and the respective garment indicator 132*a* or 134*a* will be illuminated while if a leg sleeve is attached to either port 38 or 40, system 10 identifies the cuff as discussed above and the respective garment indicator 132*b* or 134*b* will be illuminated. Therefore, system 10 provides visual indication to the operator that system 10 has identified that a foot cuff and/or a leg sleeve is attached. Combinations of a foot cuff and a leg sleeve are contemplated wherein the garment indicator for the identified garment and port combination will be illuminated by system 10 after the completion of the garment detection procedure. If no sleeves are detected by system 10 during the garment detection phase, or the detected configuration is not recognized by system 10, then a low pressure alarm will be actuated.

In one embodiment of the garment detection procedure, pressure transducer 66 measures the pressure in manifold 52 after the predetermined inflation time, which is approximately 5 seconds. Pump 50 is operated for the predetermined inflation time at a constant speed which correlates to a constant input power value of approximately 3 watts. As illustrated in Table 1 below, pressure in manifold 52 has different values for the type of inflatable garment attached to system 10 and the number of inflatable bladders in the inflatable garments. The pressures are listed in mm of Hg, but other pressure scales (e.g. torr, psi, etc.) may be used instead.

Figure 7:
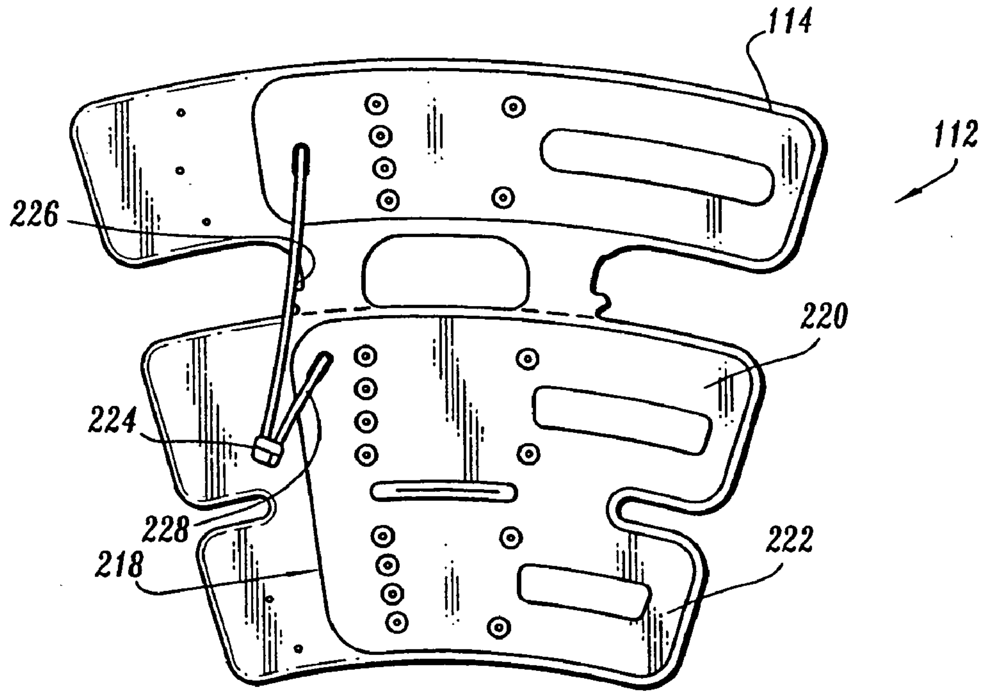
FIG. 7 is an alternate embodiment of the sleeve shown in FIG. 6.
Figure 8:
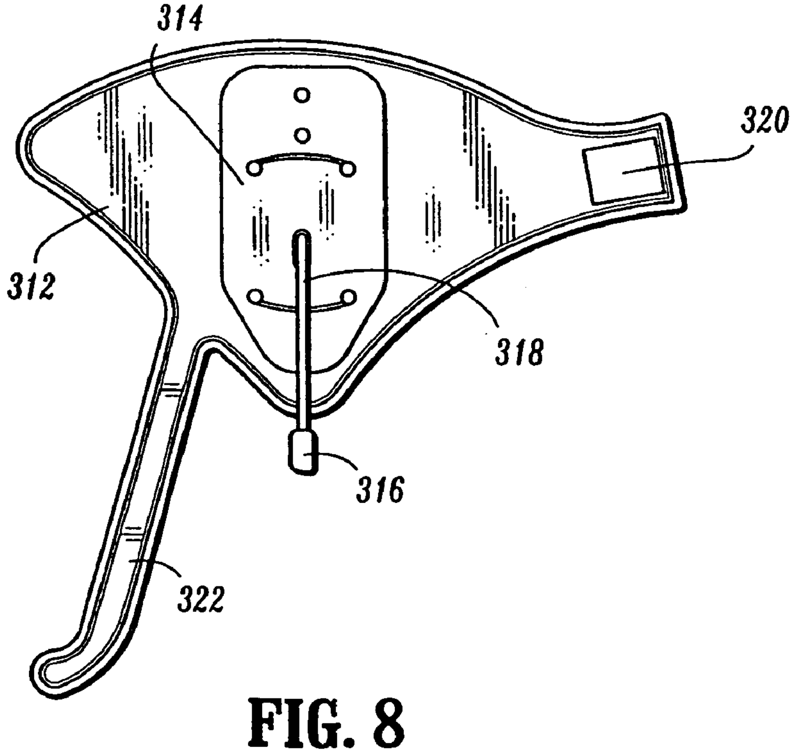
FIG. 8 is another alternate embodiment of the sleeve shown in FIG. 6.

Referring to FIGS. 5-8 and Table 1, the detection of a garment will be explained. A single port and valve combination is illustrated with other port and valve combinations operating substantially similar The steps described below can detect bladders 114, 116, or 118 (FIG. 6), bladders 114 or 218 (FIG. 7) or bladder 314 (FIG. 8). Upon completion of the self-test sequence, the detection procedure is started. The valves 58*a*-58*c* and 60*a*-60*c* are venting to the atmosphere. Controller 14 opens or energizes valve 58*a* at port 38. The controller 14 starts the pump 50 at a predetermined speed to deliver air for a predetermined amount of time through valve 58*a*, after which pressure transducer 66 measures a value of pressure at valve 58*a*. If the measured pressure value is at least than 10 mm of Hg, controller 14 compares the measured pressure to values of pressure stored in controller 14 (i.e. using a look-up table). If the controller 14 measures less than 10 mm Hg, the controller 14 signals there is no bladder connected to valve 58*a*. For example, if the measured pressure is greater than 110 mm of Hg, controller 14 identifies that a knee leg sleeve is attached to system 10. If the measured pressure is less than 110 mm of Hg, but not less than 10 mm of Hg, controller 14 identifies that a thigh leg sleeve is attached to system 10. If the measured pressure is greater than 80 mm of Hg, then controller 14 identifies that a foot cuff is attached to system 10. After detection, controller 14 opens (i.e. energizes) valve 58*a* to vent the air in the bladder. Controller 14 will select a different valve, for example, valve 58*b* and repeat the steps mentioned above.

TABLE 1

Garment Detection Pressure Measurements

| | Garment Types | | |
|---|---|---|---|
| | Thigh Leg Sleeve Manifold Pressure | Knee Leg Sleeve Manifold Pressure | Foot Cuff Manifold Pressure |
| 1 Bladder #1 | 90 | 130 | — |
| 2 Bladder #2 | 70 | 125 | 90 |
| 3 Bladder #3 | 70 | 95 | — |
| 4 Bladder #1 + Bladder #2 | 45 | 75 | |
| 5 Bladder #1 + Bladder #3 | 45 | 55 | |
| 6 Bladder #2 + Bladder #3 | 35 | 60 | |
| 7 Bladder #1 + Bladder #2 + Bladder #3 | 25 | 40 | |

Garment Detection Pressure Measurements
(Pressures measured in mmHg after 5 sec inflation @ Pump Power 3 W)

If a pressure is less than 10 mm of Hg is measured at valve 58*a*, then controller 14 will select valve 58*b* and measure a value of pressure at valve 58*b*. If the measured pressure is less than 10 mm of Hg at valve 58*b*, then controller 14 determines that no sleeve is attached to port 38. Controller 14 will repeat similar steps for port 40 using valves 60*a* and 60*b*. If one or more garments are detected, controller 14 selects the appropriate compression treatment and waits for user confirmation, as discussed hereinbelow, then controller 14 begins the compression treatment. If the user confirms the incorrect garment type, then controller 14 alarms as discussed below. There is no compression treatment during sleeve detection.

Furthermore, it is understood that the at least 10 mm Hg pressure measure is experimentally determined and is based upon the pneumatic circuit design (FIG. 5) and selected components therein, such as the pressure transducer 60, valves 58*a*-58*a* and 60*a*-60*c* and interconnecting tubing.

Once the garment type is detected at Port A, for example, the operator confirms the garment detected by system 10. The user is prompted by the lighted garment indicator (132*a*, 132*b*, 134*a*, 134*b*) on control panel 32 (FIG. 1A). The user confirms the garment identification by actuating switch 136 on port A control 132 once for the leg sleeve (default compression cycle), or actuating switch 136 a second time for the foot cuff compression. Confirmation of a garment attached to port B is substantially similar. After the user confirms the garment detection, system 10 initiates a treatment regimen. However, if the operator selected garment does not match the detected garment, then a garment mismatch error is generated for that port that is communicated to the operator via visual and/or audible indicators. Once a garment mismatch error occurs, system 10 will not initiate a treatment regimen until the operator, using the switches, selects the garment that was detected by system 10. Furthermore, the operator, during the garment detection cycle, may manually activate switches disposed on control panel 32 to select the type of garment (i.e. leg or foot) that is attached to a particular port.

Furthermore, the operator, during the garment detection cycle, may manually activate switches disposed on control panel 32 to select the type of sleeve (i.e. leg or foot) that is attached to a particular port. For a particular port, if the operator selected sleeve matches the sleeve detected by system 10, then system 10 initiates a treatment regimen. However, if the operator selected sleeve does not match the detected sleeve, then a garment mismatch error is generated for that port that is communicated to the operator via visual and/or audible indicators. Once a garment mismatch error occurs, system 10 will not initiate a treatment regimen until the operator, using the switches, selects the sleeve that was detected by system 10. In another embodiment, after the garment detection cycle is complete, system 10 will not permit the operator to change the type of sleeve attached to system 10 without restarting system 10 and repeating the garment detection cycle for the attached sleeves. For example, after the garment detection cycle is complete, if the operator adds a sleeve to an available port, system 10 will not detect the newly added sleeve and will not perform compression therapy using the newly attached (i.e. undetected) sleeve and will continue to provide the compression therapy for the sleeve detected during the garment detection cycle, while removal of a sleeve will trigger a low pressure alarm from system 10.

By providing visual and/or audible feedback (i.e. alarms or indicators) during startup, system 10 also assists in training the operator to select the correct sleeve for a compression therapy session. Specifically, system 10 reinforces correct selection of the attached sleeve or sleeves by initiating the compression therapy after the garment detection cycle is completed. If the operator selects the wrong type of sleeve for the port, system 10 will visually and/or audibly alert the operator that a mismatch has occurred. By way of example, if foot sleeves are attached to system 10, but foot mode is not selected by the operator, system 10 will alarm to alert the operator to select the correct mode for the sleeves attached. Over time, the operator will learn to select the correct sleeve during the garment detection cycle so as to prevent system 10 from alarming and initiating the desired compression therapy once the garment detection cycle is completed. Visual indicators on control panel 36 are illuminated to indicate the number of garments 114 and the types of garments (132, 134) detected. If no garments are detected by system 10 or the configuration is not recognized, then a low pressure alarm will sound.

Alternatively, compression treatment system 10 may employ one or more of the following error codes to provide audible and/or visual indicia of system error or failure. These features advantageously enhance safety to the subject during vascular therapy. Several error conditions may cause compression treatment system 10 to provide alarm and stop a particular compression cycle. It is contemplated that compression treatment system 10 may flash error indicators, sound continuous signals, etc., causing a user to reset compression treatment system 10. Controller 14 may provide an error alarm for one or more of the following error conditions: incorrect confirmation of the detected sleeve at either port, high pressure error, including those pressures detected in excess of set pressure; low pressure error, including those pressures detected below set pressure and if no sleeves are detected; system pressure error, including pressure determined within an inflation cycle outside of desired parameters; valve error; software error; pump error; vent and deflation error; battery error; and temperature error, including temperatures detected outside of specified environmental conditions.

Alternatively, thigh bladder 114 is removable from calf bladder 116. For example, calf bladder 116 is removably connected to thigh bladder 114 via a perforated attachment, see, for example, the sleeve described in U.S. patent application Ser. No. 10/784,607 to Tesluk et al., filed on Feb. 23, 2004, the entire contents of which is hereby incorporated by reference herein. For the removable thigh bladder 114, the control processor of controller 14 performs a similar sleeve detection procedure, as described above. The control processor will detect a 3-bladder sleeve due to a flow-restricting valve (not shown) fitted with connector 120. See, for example, the flow-restricting valve described in U.S. patent application Ser. No. 10/784,639 to Tordella et al., filed on Feb. 23, 2004, the entire contents of which is hereby incorporated by reference herein. The flow restricting valve simulates the backpressure created by thigh bladder 114 when there is actually no bladder connected. Thus, the conversion from a 3-bladder thigh length sleeve to a 2-bladder knee length sleeve does not significantly impact the compression parameters, and controller 14 continues vascular therapy as if thigh bladder 114 was still intact.

In an alternate embodiment, as shown in FIG. 7, sleeve 112 includes thigh bladder 114 and a unitary second bladder 218. Second bladder 218 has a calf portion 220 and an ankle portion 222. Pump 50 fluidly communicates with sleeve 112 via valve connector 224 and separate tubing 226, 228, for employment similar to that described above, including the optional removal of thigh bladder 114 via perforations or the like.

In one particular compression cycle for compression treatment system 10, the compression parameters include an 11-second inflation period for inflating bladders 114, 116, 118 followed by 60 seconds of venting for deflating bladders 114, 116, 118. The 11-second inflation period is sequential:

1) initially ankle bladder 118 is inflated for a first time period starting at 0 seconds;

2) thereafter and during the first time period, inflation of calf bladder 116 is initiated for a second time period, the initiation of the second time period coinciding with approximately 2.67 seconds duration of the first time period;

3) thereafter and during the second time period, inflation of thigh bladder 114 is initiated for a third time period, the initiation of the third time period at approximately 3.0 seconds duration of the second time period and approximately 5.67 seconds of the first time period; and 4) after 11 seconds of the first time period, bladders 114, 116, 118 vent for a minimum of 20 seconds and a maximum of 60 seconds. An example is illustrated in Table 1 below.

TABLE 2

| | Star of Sequence | End of Sequence |
|---|---|---|
| Ankle Compression: | 0 seconds | 2⅔ seconds |
| Ankle/Calf Compression: | End of Ankle | $\frac{5}{23}$ seconds |
| Ankle/Calf/Thigh Compression: | End of Ankle/Calf | 11.0 seconds |
| Decompression/Vent: | Minimum 20 seconds, maximum 60 seconds | |

It is contemplated that the vent period is measured from the end of one inflation cycle to the beginning of the next inflation cycle on leg L. It is further contemplated that both limbs of the subject may be treated and compression treatment system 10 alternates vascular therapy from leg L to the second leg. It is envisioned that the time period from the end of the inflation cycle for leg L to the initiation of the inflation cycle for the second leg can range, for example, from 4.5-24.5 seconds.

During the initial inflation cycle for treating leg L, as described above, pump 50 initiates a low default voltage so as to not over-inflate bladders 114, 116, 118 on the initial cycle. Solenoid valves 58*a*, 58*b*, 58*c* are energized to the open position, as described, such that the valves open to deliver air to ankle bladders 118, then calf bladder 116, then thigh bladder 114 of sleeve 112 using a desired cycle timing sequence. Pressure transducer 66 monitors the pressure in each of bladders 114, 116, 118 throughout the 11-second compression cycle. At the conclusion of the inflation cycle, pump 50 stops and solenoid valves 58*a*, 58*b*, 58*c* de-energize to the closed position to allow bladders 114, 116, 118 to deflate through vent ports 66*a*, 66*b*, 66*c*.

It is envisioned that if a second leg of the subject is treated for vascular therapy, solenoid valves 60*a*, 60*b*, 60*c* are energized to the open position, as described, such that the valves open to deliver air to corresponding bladders of a sleeve disposed about the second leg, similar to sleeve 112, using a desired cycle timing sequence. Pressure transducer 66 monitors the pressure in each of the corresponding bladders throughout the 11-second compression cycle. At the conclusion of the inflation cycle, pump 50 stops and solenoid valves 60*a*, 60*b*, 60*c* de-energize to the closed position to allow the corresponding bladders to deflate through vent ports 68*a*, 68*b*, 68*c*. It is further envisioned that the inflation cycle for treatment of the second leg may be initiated approximately 24.5 seconds after completion of the inflation cycle for treating leg L. This process may be reiterated for cycles pertaining to both legs. Other cycle times are contemplated.

In this embodiment, the pressures, as measured by pressure transducer 66 and the corresponding signal relayed to the control processor of controller 14, of bladders 114, 116, 118 during the inflation cycle remain gradient with the pressure of ankle bladder 118 being greater than the pressure of calf bladder 116, and the pressure of calf bladder 116 being greater than the pressure of thigh bladder 114. The end of cycle pressures, for example, include 45 mm Hg in ankle bladder 118, 40 mm Hg in calf bladder 116, and 30 mm Hg in thigh bladder 114. An example is illustrated in Table 2 below. It is contemplated that compression continues in this cyclical pattern until either compression treatment system 10 is turned off or controller 14 indicates and error code via audible or visual indicia. Other cycles pressures are contemplated.

TABLE 3

| | Thigh-Length Sleeve | Knee-Length Sleeve | Pressure (mmHg) |
|---|---|---|---|
| Ankle bladder 118 | Ankle | Ankle | 45 mmHg |
| Calf bladder 116 | Calf | Lower Calf | 40 mmHg |
| Thigh bladder 114 | Thigh | Upper Calf | 30 mmHg |

For inflation cycles subsequent to the initial inflation cycle for leg L, as described, a pressure feedback adjustment can be made pursuant to the pressure measurement taken by pressure transducer 66. At the completion of the initial inflation cycle for leg L, the end of cycle pressure in ankle bladder 118 is measured by pressure transducer 66 and compared by the control processor of controller 14 with the set pressure of 45 mm Hg. If the pressure of ankle bladder 118 is higher or lower than the set pressure, then a corresponding decrease or increase in the speed of pump 50 is required to decrease or increase pressure delivery. The pump speed adjustment is based on the following calculation:

$$\text{Adjustment}=|45-P|, \text{ where } P=\text{pressure at the ankle}$$

If the pressure is less than the set pressure, then the pump speed for the next cycle is increased by the adjustment amount. If the pressure is greater than the set pressure, then the pump speed for the next cycle is decreased by the adjustment amount. It is contemplated that the adjustment process continues even after the set pressure range is reached. It is further contemplated compression treatment system 10 may adjust for separate pump speeds for each sleeve connected to controller 14. Other sequential compression cycles are also contemplated.

In an alternate embodiment, compression treatment system 10 performs venous refill time measurement. Venous refill time (VRT) measurement is an air plethysmographic technique that determines when the veins of a limb have completely refilled with blood following a compression cycle. See, for example, the venous refill time measurement described in U.S. Pat. No. 6,231,532 to Watson et al., the entire contents of which is hereby incorporated by reference herein. The VRT minimizes the amount of time that the blood remains stagnant inside the veins. The VRT will be substituted for the default rest time (60 seconds) as long as the VRT is between 20 and 60 seconds. If the VRT is less than 20 seconds then the default of 20 seconds is used. If the VRT is greater than 60 seconds then the maximum of 60 seconds is used. The VRT measurement is made when the system first reaches set pressure and once every 30 minutes thereafter. It is contemplated that the VRT technique and algorithm can be used for both sleeve and foot compression.

The VRT measurement uses an air plethysmographic technique where a low pressure is applied to the calf bladders. As the veins fill with blood, the pressures in the calf bladders increase until a plateau is reached. The time that it takes for the pressure to plateau is the VRT. If two sleeves are connected to controller 14, then the VRT is determined separately for each limb being compressed and the greater of the two measurements is used as the new vent time of the compression cycle. The VRT measurement for each sleeve is made as each particular sleeve reaches set pressure independently. However, the vent time is not updated until VRT measurements have been calculated for both sleeves.

For example, compression treatment system 10 may employ the VRT measurement after the system initiates vascular therapy. Subsequently, after 30 minutes have elapsed, a VRT measurement will be taken on the next full inflation cycle. After any of the sleeves described above inflates, the bladder(s) of the particular sleeve are vented down to zero as in the default inflation cycle.

It is contemplated that a selected bladder pressure is monitored and the vent to the bladder is closed when the pressure falls to 5-7 mm Hg. If the pressure in the bladder is 5-7 mm Hg on a current cycle then a VRT measurement is taken. If the pressure in the bladder does not vent down to 5-7 mm Hg then the vent time will remain at its current value and another measurement will be made in 30 minutes. If an error occurs, a corresponding alarm provides audible and/or visual indicia.

The VRT measurement algorithm determines when the pressures in the selected bladders plateau after compression. The VRT will be determined separately for both legs. The longer of the two refill times will be used as the new vent time. If compression is applied to only one leg, the VRT for that leg is used as the new vent time. The VRT measurement algorithm initiates with a time counter started from the end of the inflation cycle, which occurs after the selected bladder reaches 5-7 mm Hg (enough pressure to cause the bladder to remain in contact with the surface of the leg) and the venting is stopped. The VRT measurement initiates with the time counter started from the end of the inflation cycle.

The pressure in the selected bladder is then monitored. By way of example, the pressure is monitored with a 10-second, moving sample window. The window moves in 1-second intervals. When the difference between the first and last values in the window is less than approximately 0.3 mm Hg the curve has reached its plateau. The VRT measurement is considered done, and the time interval is determined. The end of the window is considered to be the point at which the venous system in the limbs has refilled.

Independent of the VRT measurement, the selected bladder is allowed to vent for at least 15 seconds before the next compression cycle on that same limb is started. As a safety factor, 5 seconds are added to the measured refill time so the limb is not compressed too quickly. It is contemplated that the vent time may be equivalent to the measured refill time plus 5 seconds. For example, as a result of patient movement, the standard deviation in the sample window may be too high making the measurement erroneous. At this point, the calculation is discarded and the old value of the VRT is used. The VRT measurement is considered erroneous if at any time during the measurement, the pressure in the selected bladder is below 2 mmHg, the calculation is discarded, and the old value of VRT is used. This may occur if there is a leak in the system. It is contemplated that if the pressure is greater than 20 mmHg at any time during the VRT measurement the old value of the VRT is used. It is further contemplated that if the VRT calculation is done for both legs, the longer VRT of both legs is used. It is envisioned that if the VRT is calculated to be greater than 60 seconds, a value of 60 seconds is used. If the VRT is calculated to be less than 20 seconds, a value of 20 seconds is used.

Alternatively, compression treatment system 10 may employ one, a plurality or all of the following error codes to provide audible and/or visual indicia of system error or failure. These features advantageously enhance safety to the subject during vascular therapy. Several error conditions may cause compression treatment system 10 to provide alarm and stop a particular compression cycle. It is contemplated that compression treatment system 10 may flash error indicators, sound continuous signals, etc., causing a user to reset compression treatment system 10. Controller 14 may provide an error alarm for one, a plurality or all of the following error conditions: high pressure error, including those pressures detected in excess of set pressure; low pressure error, including those pressures detected below set pressure and if no sleeves are detected; system pressure error, including pressure determined within an inflation cycle outside of desired parameters; valve error; software error; pump error; vent and deflation error; battery error; and temperature error, including temperatures detected outside of specified environmental conditions.

In an alternate embodiment, as shown in FIG. 8, compression treatment system 10, similar to that described above, includes a foot sleeve 312 configured to provide vascular therapy to the foot of the subject. Foot sleeve 312 includes a bladder 314 that is inflated with air to provide application of pressure to the foot and then deflated. See, for example, the sleeve described in U.S. patent application Ser. No. 10/784,604 to Gillis et al., filed on Feb. 23, 2004, the entire contents of which is hereby incorporated by reference herein.

Pump 50 fluidly communicates with foot sleeve 312. Sleeve 312 includes a valve connector 316 that mates with mating connector 42, which is connected to port 40 via tubing 44. Valve connector 316 fluidly communicates with bladder 314 of sleeve 312 via tubing 318. Thus, this configuration facilitates fluid communication between bladder 314 and pump 50. Foot sleeve 312 wraps about the side portions of the foot via a hook and loop type connector flap 320 that transverses the instep of the foot and a hook and loop type connector ankle strap 322.

Upon completion of the self-test sequence compression for treatment system 10, similar to that described, controller 14 begins the sleeve detection procedure to determine the type(s) of sleeves attached to ports 38, 40. With regard to foot sleeve 312, back pressure is detected by the control processor of controller 14 corresponding to bladder 314, which is connected to outlet port 40*b*. It is contemplated that compression treatment system 10 may treat the foot of a second leg of a subject with foot sleeve 312 and also treat leg L, as described above, in alternate inflation cycles.

In one particular exemplary compression cycle for foot sleeve 312, the compression parameters include a 5-second inflation period followed by 60 seconds of venting. An example is illustrated in Table 3 below.

TABLE 4

| | Start of Sequence | End of Sequence |
|---|---|---|
| Foot Compression: | 0 Seconds | 5.0 seconds |
| Decompression/Vent: | Minimum 20 seconds, maximum 60 seconds | |

It is contemplated that the vent period is measured from the end of one inflation cycle to the beginning of the next inflation cycle on the foot of the subject. It is further contemplated that both limbs of the subject may be treated and compression treatment system 10 alternates vascular therapy from leg L to the second leg. It is envisioned that the time period from the end of the inflation cycle for leg L to the initiation of the inflation cycle for the second leg can range from 7.5-27.5 seconds.

During the initial inflation cycle for treating the foot of the subject, as described above, pump 50 initiates a low default voltage so as to not over-inflate bladder 314 on the initial cycle. Solenoid valve 60*b* is energized to the open position, as described, such that the valve opens to deliver air to bladder 314 using a desired cycle timing sequence. Pressure transducer 66 monitors the pressure in bladder 314 throughout the 5-second compression cycle. At the conclusion of the inflation cycle, pump 50 stops and solenoid valve 60*b* de-energizes to the closed position to allow bladder 314 to deflate through vent port 68*b*.

It is envisioned that if a second foot of the subject is treated for vascular therapy, solenoid valve 58*b* is energized to the open position, as described, such that the valve opens to deliver air to a corresponding bladder of a foot sleeve disposed about the other leg, similar to foot sleeve 312, using a desired cycle timing sequence. For example, pressure transducer 66 monitors the pressure in the corresponding bladder throughout the 5-second compression cycle. At the conclusion of the inflation cycle, pump 50 stops and solenoid valve 58*b* de-energizes to the closed position to allow the corresponding bladder to deflate through vent port 66*b*. It is further envisioned that the inflation cycle for treatment of the second foot may be initiated approximately 27.5 seconds after completion of the inflation cycle for treating the foot treated by foot sleeve 312. This process may be reiterated for cycles pertaining to both feet, or in the alternative, for foot sleeve of a first leg and a leg sleeve of a second leg. It is contemplated that compression treatment system 10 may provide alternating compression to any combination of a sleeve and a foot garment and that if such a combination is employed, then, for example, a 6-second buffer of additional vent timing is added to all vent periods after the foot inflation cycle so that the overall timing is consistent with the default sleeve compression parameters. Other cycles times are contemplated.

In this embodiment, the target pressure, as measured by pressure transducer 66 and the corresponding signal relayed to the control processor of controller 14, of bladder 314 is, for example, 130 mm Hg. It is contemplated that compression continues in this cyclical pattern until either compression treatment system 10 is turned off or controller 14 indicates an error code via audible or visual indicia.

For inflation cycles subsequent to the initial inflation cycle for foot sleeve 312 described, a pressure feedback adjustment can be made pursuant to the pressure measurement taken by pressure transducer 66. At the completion of the initial inflation cycle for foot sleeve 312, the end of cycle pressure in bladder 314 is measured by pressure transducer 66 and compared by the control processor of controller 14 with the set pressure of 130 mm Hg. If the pressure of bladder 314 is higher or lower than the set pressure, then a corresponding decrease or increase in the speed of pump 50 is required to decrease or increase pressure delivery. The pump speed adjustment is based on the following calculation:

$$\text{Adjustment}=|130-P|,\ \text{where } P=\text{pressure at the foot}$$

If the pressure is less than the set pressure, then the pump speed for the next cycle is increased by the adjustment amount. If the pressure is greater than the set pressure, then the pump speed for the next cycle is decreased by the adjustment amount. It is contemplated that the adjustment process continues even after the set pressure range is reached. It is further contemplated that compression treatment system 10 may adjust for separate pump speeds for each sleeve connected to controller 14. Other sequential compression cycles are also contemplated.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for detecting the presence of a garment connected to a port comprising the steps of:

(a) selecting and opening at least one valve from a plurality of valves;

(b) providing air through at least one valve to a bladder operably connected to said selected valve;

(c) measuring a value of pressure at said selected valve;

(d) identifying at least one garment connected to said port based upon the measured value of pressure at said selected valve;

(e) closing the selected valve to deflate the bladder connected to the selected valve;

(f) confirming the identification of said at least one identified garment by manually activating a switch located at a control panel;

(g) activating a compression cycle for the detected and confirmed at least one garment;

(h) actuating an alarm, if the at least one garment is not confirmed and inhibiting an inflation cycle in said garment.

2. The method of claim 1, wherein in step (f), the confirming of the identification of said at least one garment is determined by:

flashing a light on said control panel.

3. The method of claim 1, wherein in step (c), the measured pressure is at least 10 mm HG.

* * * * *